United States Patent

Ribka et al.

[11] 3,957,756
[45] May 18, 1976

[54] PREPARATION OF SUBSTITUTED UREAS

[75] Inventors: Joachim Ribka, Offenbach (Main-Burgel); Manfred Schon, Offenbach (Main), both of Germany

[73] Assignee: Cassella Farbwerke Mainkur Aktiengesellschaft, Germany

[22] Filed: Oct. 9, 1973

[21] Appl. No.: 404,269

[30] Foreign Application Priority Data
Oct. 13, 1972    Germany............................ 2250134

[52] U.S. Cl..................... 260/239.3 R; 260/293.65; 260/544 C; 260/293.69; 260/326.4; 260/293.71; 260/293.76; 260/326.25; 260/293.86; 260/553 A; 260/553 E; 260/326.37; 260/239 BE; 260/31.6; 260/31.2 N

[51] Int. Cl.².................................... C07D 223/10

[58] Field of Search.............. 260/239.3 R, 293.65, 260/326.25, 553 A, 553 E, 293.69, 293.71

[56] References Cited
UNITED STATES PATENTS

| | | | |
|---|---|---|---|
| 2,682,526 | 6/1954 | Flory............................ | 260/239.3 R |
| 3,804,291 | 2/1967 | Dachs et al. ................ | 260/239.3 R |

Primary Examiner—Natalie Trousoe
Assistant Examiner—Robert T. Bond
Attorney, Agent, or Firm—Connolly and Hutz

[57] ABSTRACT

A process for preparing a substituted urea of the formula

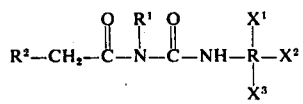

wherein $R^1$ taken separately is alkyl having 1 to 8 carbon atoms, alkenyl having 3 to 8 carbon atoms, cycloalkyl having 5 to 6 carbon atoms or aryl having 6 to 12 carbon atoms; $R^2$ taken separately is hydrogen, alkyl having 1 to 18 carbon atoms, alkenyl having 2 to 18 carbon atoms, aralkyl having 7 to 14 carbon atoms or aryl having 6 to 12 carbon atoms or $R^1$ and $R^2$ taken together form a polymethylene bridge having 2 to 10 carbon atoms; R is a tetravalent alkane radical having 1 to 6 carbon atoms, a tetravalent alkene radical having 3 to 8 carbon atoms, a tetravalent cycloalkane radical having 5 to 6 carbon atoms, a tetravalent aralkane radical having 7 to 14 carbon atoms or a tetravalent aryl radical having 6 to 12 carbon atoms and $X^1$, $X^2$ and $X^3$ are each hydrogen or

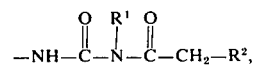

said process comprising the steps of reacting an N-(1-chloro-1-alkenyl)-carbamic acid chloride of the formula

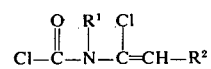

with an amine of the formula

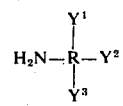

wherein $Y^1$, $Y^2$ and $Y^3$ are each hydrogen or amino in the presence of an alkali metal hydroxide at a temperature of from 5° to 60°C. and in a molar ratio of n mols of said carbamic acid chloride reactant and n mols of said alkali metal hydroxide per mol of said amine reactant, n being a number equal to the number of the amino substituents on said amine reactant, and then hydrolyzing the resulting intermediate at a temperature of from 20° to 100°C. to obtain said substituted urea of said formula, and its utility as masked isocyanate in the preparation of lacquers and coating materials.

4 Claims, No Drawings

PREPARATION OF SUBSTITUTED UREAS

This invention relates to a process for producing urea derivatives of the formula

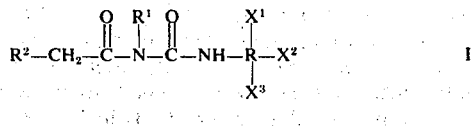
                    I wherein $R^1$ taken separately is alkyl having 1 to 8 carbon atoms, alkenyl having 3 to 8 carbon atoms, cycloalkyl having 5 to 6 carbon atoms or aryl having 6 to 12 carbon atoms; $R^2$ taken separately is hydrogen, alkyl having 1 to 18 carbon atoms, alkenyl having 2 to 18 carbon atoms, aralkyl having 7 to 14 carbon atoms or aryl having 6 to 12 carbon atoms or $R^1$ and $R^2$ taken together form a polymethylene bridge having 2 to 10 carbon atoms; R is a tetravalent alkane radical having 1 to 6 carbon atoms, a tetravalent alkene radical having 3 to 8 carbon atoms a tetravalent cycloalkane radical having 5 to 6 carbon atoms a tetravalent aralkane radical having 7 to 14 carbon atoms or a tetravalent aryl radical having 6 to 12 carbon atoms and $X^1$, $X^2$ and $X^3$ are each hydrogen or

said process comprising the steps of reacting an N-(1-chloro-1-alkenyl)-carbamic acid chloride of the formula

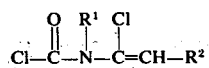
                    II with an amine of the formula

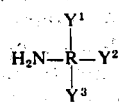
                    III wherein $Y^1$, $Y^2$ and $Y^3$ are each hydrogen or amino in the presence of an alkali metal hydroxide at a temperature of from 5° to 60°C. and in a molar ratio of $n$ mols of said carbamic acid chloride reactant and $n$ mols of said alkali metal hydroxide per mol of said amine reactant, $n$ being a number equal to the number of the amino substituents on said amine reactant, and then hydrolyzing the resulting intermediate at a temperature of from 20° to 100°C. to obtain said substituted urea of said formula.

Preferably, $R^1$ taken separately is alkyl having 1 to 4 carbon atoms, alkenyl having 3 to 4 carbon atoms, cycloalkyl having 5 to 6 carbon atoms or phenyl; $R^2$ taken separately is hydrogen, alkyl having 1 to 8 carbon atoms, alkenyl having 2 to 8 carbon atoms, benzyl, phenethyl or phenyl or $R^1$ and $R^2$ taken together form a polymethylene bridge having 4 to 6 carbon atoms and R is a tetravalent alkane radical having 1 to 6 carbon atoms, a tetravalent alkene radical having 3 to 4 carbon atoms, a tetravalent cycloalkane radical having 5 to 6 carbon atoms, a tetravalent aralkane radical having 7 to 14 carbon atoms or a tetravalent benzene radical.

The N-(1-chloro-1-alkenyl)-carbamic acid chloride reactants of the formula

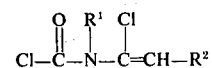
                    II wherein $R^1$ and $R^2$ are as aforesaid and may be prepared by introducing a compound of the formula

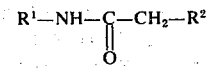
                    IV into a phosgene solution containing at least 2 mols of phosgene for each mol of compound IV and maintaining a temperature of −20° to 50°C. in said solution during the introduction of compound IV. Typical examples of such preparations are included hereinafter.

The compounds of formula III are mono-, di-, tri- and tetraamines. The monoamines and diamines are preferred. With the use of monoamines wherein $Y^1$, $Y^2$ and $Y^3$ are each hydrogen, $X^1$, $X^2$ and $X^3$ are hydrogen in the final product of formula I. With the use of diamines wherein $Y^1$ and $Y^3$ are hydrogen and $Y^2$ is $NH_2$ in formula III, the products of formula I are of the formula

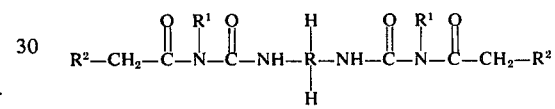

Particularly preferred mono- and diamines include, for example, ethylamine, propylamine, allylamine, butylamine, crotylamine, amylamine, hexylamine, ethylene diamine, propylene-diamine-1,3, butylene-diamine-1,4, pentamethylene-diamine-1,5, hexamethylene-diamine-1,6, cyclohexylamine, 3-aminomethyl-3,5,5-trimethylcyclohexylamine, benzylamine, phenethylamine, aniline, α-naphthylamine, β-naphthylamine, 3-aminobenzylamine, 4-aminobenzylamine, 4,4′-diaminodiphenylmethane, o-, m- and p-phenylene-diamine and 1,4-, 1,5- and 1,8-diaminonaphthalene.

Radicals defining $R^1$, $R^2$ and R may also be substituted by moieties which do not interfere with the reaction conditions of the claimed process. Such substituents include, for example, halogen, preferably chlorine or bromine, nitro, alkyl having 1 to 4 carbon atoms, phenoxy and alkoxy having 1 to 4 carbon atoms.

Preferably, the amine reactant of formula III is dissolved or suspended in the aqueous phase and reacted with the N-(1-chloro-1-alkenyl)-carbamic acid chloride of formula II in the presence of alkali metal hydroxide in specified quantities. The reaction is exothermic and preferably carried out at temperatures of 5° to 60°C. The following conversion takes place:

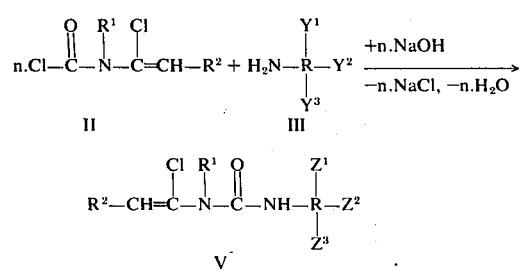

wherein $Z^1$, $Z^2$ and $Z^3$ are hydrogen or

At higher temperatures, the second chlorine atom of the reactant of formula II may also react with the amine reactant.

In the above reaction, molar ratios of the reactants of formula II and formula III and the alkali metal hydroxide are selected in such a manner that $n$ mols of a carbamic acid chloride of formula II and $n$ mols of the alkali metal hydroxide reactant react with each mol of the amine reactant of formula III which is present, $n$ being the number of amino groups of the amine reactant of formula III.

Although all alkali metal hydroxides are suitable for purposes of the present invention, sodium hydroxide is preferred. Additionally and as those skilled in the art will appreciate, any other alkaline reacting compound capable of binding HCl by-product may be employed. Indeed, the alkali metal hydroxide may be substituted by an equimolar quantity of an amine of formula III.

The intermediate products of formula V may, in some instances, be isolated. However, in many instances, they are unstable and decompose with the liberation of HCl when one attempts to dry them. However, in order to obtain the final product of formula I, isolation of the intermediate product of formula V is not required. Thus, the hydrolysis of the intermediate product of formula V may be carried out by heating the aqueous suspension thereof at a temperature of from 20° to 120°C., preferably 70° to 95°C. Such heating is preferably carried out in the presence of alkali metal hydroxide as hydrogen chloride acceptor. However, such acceptor need not be present. Particularly when working with relatively large quantities, it is advantageous to introduce the intermediate product of formula V or the aqueous suspension thereof stepwise into hot water which contains sufficient alkali metal hydroxide to function as hydrogen chloride acceptor.

The hydrolysis step for the present process proceeds as follows:

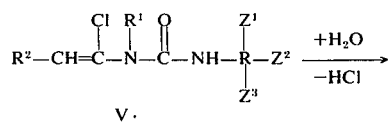

V.

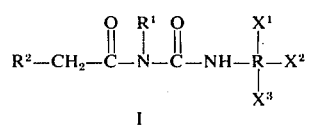

I

While, in many instances, hydrolysis may be carried out at temperatures from 20° to 100°C. and preferably from 70° to 95°C., in some instances, temperatures of up to 120°C. are required. This requires the use of super-atmospheric pressure or hydrolysis must be carried out in a suitable high boiling solvent. For example, in the reaction of ethylene diamine with 1-aza-2-chlorocycloheptene-2-carboxylic acid chloride-(1), a stable intermediate product which may be recrystallized from alcohol is obtained. Hydrolysis to ethylene-1,2-bis-carbamidocaprolactam is successful at about 120°C. in hydrous dimethylformamide.

The substituted ureas of formula I are masked mono- and polyisocyanates and are produced by the process of the present invention in a state of high purity with yields of 75–95 % of theory. As is known, these masked isocyanates are valuable in the preparation of synthetic materials, particularly lacquers and coatings, because they are capable of splitting off a reactive isocyanate if they are heated to temperatures of 160°C. or above. Distillation of the masked mono- and polyisocyanates produced by the instant process yields the corresponding free mono- and polyisocyanates. For example, product VI obtained from a monoamine according to the instant invention yields the amide VII (which is a lactam if $R^1$ and $R^2$ taken together form a polymethylene bridge) and the reactive isocyanate VIII.

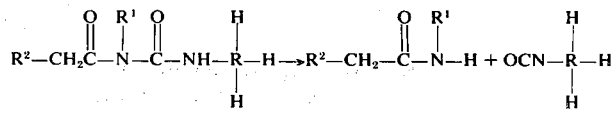

VI                    VII           VIII

The cleavage is performed by heating to 160°C. or higher temperatures. It is well known in the art to prepare heat-setting lacquers, especially pulverulent heat-setting coating materials by mixing a polyester with a di-, tri- or tetra-isocyanate having its isocyanate groups masked with heat-cleavable groups especially lactam groups. Such pulverulent heat-setting coating materials are applied onto the surface to be protected by operations, such as dusting or electrostatic spraying and coating is produced by heating or baking. Temperatures between 160° and 200°C. and baking times of between 10 and 60 minutes are generally employed.

During the heating the free isocyanate groups split off, react with the polyester in known manner, thus yielding elastic coatings having smooth and highly glossy surfaces together with a good hardness, weather, temperature and chemical resistance. The preparation of the polyester and the preparation of the heat-setting coating materials are described for instance in Belgian Patent No. 789,007, German Patent application laid open to public inspection No. 2,146,841, U.S. Pat. No. 2,982,754, British Patent No. 718,822 or British Patent No. 767,017.

EXAMPLE 1

A. General Description of Exemplary Procedure for Carrying Out The Process of This Invention There is dissolved or suspended in 50 ml water, which contains 4 g sodium hydroxide (0.1 mol), 0.1 mol of a monoamine, 0.05 mol of a diamine, 0.033 mol of a triamine or 0.025 mol of a tetramine. Then at 20° to 40°C. internal temperature, 0.1 mol of an N-(1- chloro-1-alkenyl)-carbamic acid chloride are added dropwise within about 30 minutes. Stirring then proceeds 30 to 300 minutes more at a temperature of 20° to 40°C. and subsequently the finely divided suspension is introduced in increments within about 30 minutes into a solution of 4 g sodium hydroxide (0.1 mol) in 25 ml water, which is vigorously agitated at 95°C. internal temperature. Stirring proceeds another 45 minutes at 95°C. internal temperature. The flask contents are then adjusted to pH 7 and cooled to room temperature. After removal from the reaction mixture, the product is washed with water and dried.

B. Preparation of N-(1-Chloro-1-Alkenyl)-Carbamic Acid Chlorides

A solution of 297 g phosgene (about 3 mol) in 250 ml toluene is cooled to −10°C. and during agitation mixed with 1 mol of a lactam or a secondary aliphatic acid amide (if necessary dissolved in toluene) in such a manner that the internal temperature does not rise above −5°C.

During this procedure, a white deposit is formed with vigorous gas evolvement. Upon the addition of the amide or lactam, stirring proceeds 1 hour at −5° to −10°C. Subsequently, the reaction mixture is warmed up gradually to room temperature and a clear solution results. The flask contents are then heated 5 hours more to 70°C. during which time excess phosgene escapes. After removing the solvent, the residue is distilled under vacuum, the N-(1-chloro-1-alkenyl)-carbamic acid chloride passing over.

EXAMPLE 2

In accordance with the procedure described in Example 1, 7.3 g n-butylamine are reacted with 19.4 g 1-aza-2-chlorocycloheptene-2-carboxylic acid chloride-(1). After the reaction, the oil layer is taken up in ether and after separation, the solvent is distilled off under vacuum. Obtained was N-butylcarbamoylcaprolactam having the formula

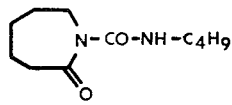

Yield: 76% of theory
Boiling point: 50°C./30 torr

| Analysis: | | C | H | N |
|---|---|---|---|---|
| | Calculated | 62.2% | 9.4% | 13.2% |
| | Found | 61.7% | 9.2% | 13.0% |

For the preparation of the starting product, 113.2 g ε-caprolactam are reacted in accordance with the procedure described in Example 1. Obtained is 1-aza-2-chlorocycloheptene-2-carboxylic acid chloride-(1).
Yield: 85% of theory
Boiling point: 96°C./1.5 torr

| Analysis: | | Cl | N |
|---|---|---|---|
| | Calculated | 36.6% | 7.2% |
| | Found | 36.5% | 7.2% |

EXAMPLE 3

According to the procedure described in Example 1, 3.7 g propylene-diamine-1,3 are reacted with 19.4 g 1-aza-2-chlorocycloheptene-2-carboxylic acid chloride-(1). Obtained is propylene-1,3-bis-carbamoylcaprolactam of the formula

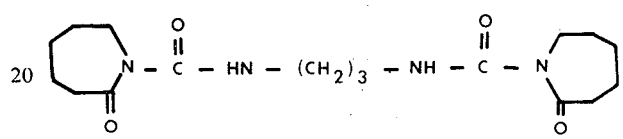

Yield: 87% of theory
Melting point: 104°–106°C.

| Analysis: | | C | H | N |
|---|---|---|---|---|
| | Calculated | 57.9% | 7.95% | 15.9% |
| | Found | 58.3% | 7.7% | 16.0% |

EXAMPLE 4

In accordance with the procedure described in Example 1, 5.8 g hexamethylene diamene were reacted with 19.4 g 1-aza-2-chlorocycloheptene-2-carboxylic acid chloride-(1). Obtained is hexamethylene-1,6-bis-carbamoylcaprolactam of the formula

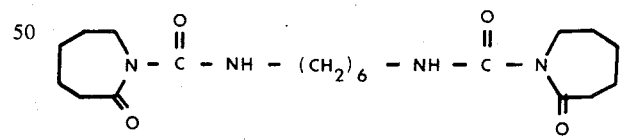

Yield: 95% of theory
Melting point: 84°–86°C.

| Analysis: | | C | H | N |
|---|---|---|---|---|
| | Calculated | 60.9% | 8.6% | 14.2% |
| | Found | 60.5% | 8.6% | 13.9% |

EXAMPLE 5

In accordance with the procedure described in Example 1, 11.6 g hexamethylene diamine and 38.8 g 1-aza-2-chlorocycloheptene-2-carboxylic acid chloride-(1) are reacted. The chlorine-containing intermediate product of the formula

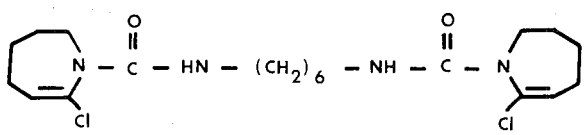

however, is separated, washed well and dried under vacuum at 50°C. by the passage of an air current at about 100 torr. HCl is split off. After drying, there are obtained 37.4 g hexamethylene-1,6-bis-carbamoylcaprolactam (97% of theory) having a melting point of 85°–87°C.

EXAMPLE 6

In accordance with the procedure described in Example 1, 5.8 g hexamethylene diamine are reacted with 16.6 g 2-chloro-Δ²-pyrrolidine-1-carboxylic acid chloride. Obtained is hexamethylene-1,6-bis-carbamoylpyrrolidone-(2) of the formula

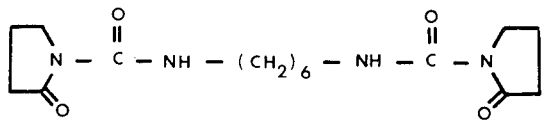

Yield: 82% of theory
Melting point: 87°–89°C.

| Analysis: | | C | H | N |
|---|---|---|---|---|
| | Calculated | 56.8% | 7.7% | 16.6% |
| | Found | 56.3% | 7.4% | 16.3% |

For the preparation of the acid chloride starting product, 85.1 g pyrrolidone-(2) are reacted in accordance with the procedure described in Example 1. Obtained is 2-chloro-Δ²-pyrrolidine-1-carboxylic acid chloride.
Yield: 58% of theory
Boiling point: 125°C./10 torr

| Analysis: | | Cl | N |
|---|---|---|---|
| | Calculated | 42.8% | 8.4% |
| | Found | 43.2% | 8.1% |

EXAMPLE 7

In accordance with the procedure described in Example 1, 5.8 g hexamethylene diamine are reacted with 21.6 g N-1-chlorovinyl-N-phenylcarboxylic acid chloride. Obtained is 1,6-bis-(N'-phenyl-N'-acetyl-ureido)-hexane of the formula

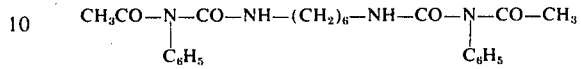

which may be recrystallized from toluene.
Yield: 75% of theory
Melting point: 114°–116°C.

| Analysis: | | C | H | N |
|---|---|---|---|---|
| | Calculcated | 65.6% | 6.8% | 12.8% |
| | Found | 66.3% | 6.6% | 12.2% |

The necessary acid chloride starting product is prepared by incrementally mixing a solution of 297 g phosgene in 600 ml anhydrous dioxane at −5°C. while stirring with 135.2 g acetanilide. Then the mixture is warmed up gradually to room temperature and stirred until a clear solution results (about 3 days). Subsequently, the flask contents are heated 5 hours to 70°C. and the residue fractionally distilled after removing the solvent. Obtained are 162 g (74% of theory) N-1-chlorovinyl-N-phenylcarbamic acid chloride having a boiling point of 117°C. at 2 torr.

| Analysis: | | Cl | N |
|---|---|---|---|
| | Calculated | 32.9% | 6.5% |
| | Found | 32.3% | 6.7% |

EXAMPLE 8

In accordance with the procedure of Example 1, 9.3 g freshly distilled aniline are reacted with 19.4 g 1-aza-2-chlorocycloheptene-2-carboxylic acid chloride-(1). Obtained is N-(phenylcarbamoyl)-caprolactam of the formula

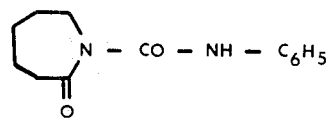

which may be recrystallized from ethanol.
Yield: 78% of theory
Melting point: 68°–70°C.

| Analysis: | | C | H | N |
|---|---|---|---|---|
| | Calculated | 67.2% | 6.9% | 12.1% |
| | Found | 67.6% | 6.8% | 12.3% |

The 1-aza-2-chlorocycloheptene-2-carboxylic acid chloride is prepared by introducing phosgene, up to the saturation point, into 550 ml chlorobenzene with stirring and at 45°C. Saturation is achieved after about 30 minutes and is recognized because phosgene flows back vigorously from the reflux cooler which is maintained at a temperature of about −10°C. During further stirring and introduction of phosgene, 283 g melted ε-caprolactam at about 100°C. is added dropwise in such a manner that a vigorous reflux of phosgene sets in at a bath temperature of 50°C. and an internal temperature of 45°C. After the addition of ε-caprolactam, which takes place in about 2½ hours, phosgene is introduced for 15 minutes more at a bath temperature of 50°C. and stirring is continued for 7 hours. Then the reaction mixture is slowly heated to 100°C. and under slowly increasing vacuum, the chlorobenzene is drawn off and finally 440 g 1-aza-2-chlorocycloheptene-2-carboxylic acid chloride (b.p. 96°C./1.5 torr) is distilled over at a bath temperature of 125° to 140°C.

Yield: 90.7% of theory

EXAMPLE 9

In accordance with the description of Example 1, 9.3 g freshly distilled aniline are reacted with 16.8 g N-1-chloropropenyl-N-methylcarbamic acid chloride.

Obtained is N-methyl-N'-phenyl-N-propionyl urea, which may be recrystallized from ethanol.

Yield: 81% of theory
Melting Point: 97°–99°C.

| Analysis: | | C | H | N |
|---|---|---|---|---|
| | Calculated | 64.0% | 6.8% | 13.6% |
| | Found | 64.5% | 6.6% | 13.5% |

For the preparation of the necessary acid chloride starting product, 87.1 g N-methylpropionic acid amide are reacted in accordance with the description given in Example 1. Obtained is N-1-chloropropenyl-N-methylcarbamic acid chloride.

Yield: 44.6% of theory
Boiling point: 76°–77°C./9 torr

| Analysis: | | Cl | N |
|---|---|---|---|
| | Calculated | 42.3% | 8.3% |
| | Found | 41.7% | 8.8% |

EXAMPLE 10

In accordance with the procedure given in Example 1, 5.4 g m-phenylene diamine are reacted with 19.4 g 1-aza-2-chlorocycloheptene-2-carboxylic acid chloride-(1). Obtained is 1,3-bis-(N-caprolactamylcarbonamide)-benzene of the formula

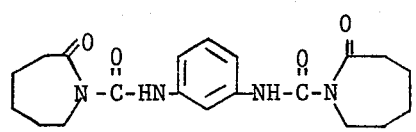

which may be recrystallized from ethanol.

Yield: 75% of theory
Melting point: 174°–176°C.

| Analysis: | | C | H | N |
|---|---|---|---|---|
| | Calculated | 62.1% | 6.7% | 14.5% |
| | Found | 62.0% | 6.6% | 14.8% |

EXAMPLE 11

Ethylene diamine (3 g) is dissolved in 50 ml water containing 4 g NaOH (0.1 mol). There is added dropwise thereto at 20°–40°C. internal temperature within about 30 minutes, 19.4 g 1-aza-2-chlorocycloheptene-2-carboxylic acid chloride. Stirring is continued at the same temperature for 30 minutes and the product is recovered at room temperature. The still moist chlorine-containing intermediate product is introduced in increments into 20 ml dimethylformamide, which is vigorously stirred at 120°C. internal temperature. Further stirring continues at 120°C. until the evolvement of hydrochloric acid ceases (about 2 hours). After hot filtering, the clear solution is extensively concentrated under vacuum. After the addition of 50 ml water, it is adjusted with sodium hydroxide to pH 7, the product is recovered washed with water and dried. Obtained is ethylene-1,2-bis-carbamoylcaprolactam in a yield of 77% of theory and a melting point of 146°–148°C.

| Analysis: | | C | H | N |
|---|---|---|---|---|
| | Calculated | 56.8% | 7.7% | 16.6% |
| | Found | 56.2% | 7.7% | 16.3% |

EXAMPLE 12

Preparation of Lacquers and Coatings from Compounds of Formula I

Hexamethylene-1,6-bis-carbamoylcaprolactam (65 g prepared in accordance with Example 4) is heated to 120°C. There are added to the melt 35 g of the polyester whose preparation is described below, as well as 2 g dibutyl tin dilaurate and 35 g titanium dioxide. This mixture is stirred 1 hour at 100°C. Upon cooling, a viscous mass is obtained, which, after some time, becomes solid and millable.

After milling in a beater, ball or oscillating mill and subsequent filtering to a grain size of 30–100μ, the pulverulent coating agent is dusted onto a metal sheet and heated up at 180°C. for 30 minutes. Obtained was a coating film, having 70μ thickness, with the following properties:

| | |
|---|---|
| Erichsen value (DIN 53156) | 10 mm |
| Grid sections (DIN 53151) | 0 |
| Impact test according to Gardner (with Erichsen apparatus Type 304) | 0.5 kpm |
| Degree of glazing according to Lange | >100% |
| Weather stability in weather meter (unfiltered carbon arc) Decrease in brilliance after 500 hrs. | from 100 to 84% |
| Ford xylene test | no reaction |

The polyester used above is prepared by melting in a reaction vessel, provided with stirrer, descending cooler and gas inlet pipe, 626 g pentaerythrite and 137 g hexane diol-1,6. Then there are introduced 500 g of a mixture consisting of 70% by weight isophthalic acid and 30% by weight terephthalic acid under an inert gas stream. The reaction mixture is then heated to 220°–240°C. during stirring and further introduction of inert gas. After about 20 hours, a clear yellowish melt results. The acid number is 1–2 and the OH number is 620 mg KOH/g. The polyester is cooled, rendered into small pieces and further processed in this form.

What is claimed is:

1. A process for preparing a substituted urea of the formula

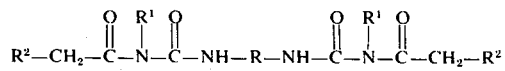

wherein $R^1$ taken separately is alkyl having 1 to 8 carbon atoms, alkenyl having 3 to 8 carbon atoms, cycloalkyl having 5 to 6 carbon atoms or aryl having 6 to 12 carbon atoms; $R^2$ taken separately is hydrogen, alkyl having 1 to 18 carbon atoms, alkenyl having 2 to 18 carbon atoms, aralkyl hydrocarbon having 7 to 14 carbon atoms or aryl hydrocarbon having 6 to 12 carbon atoms or $R^1$ and $R^2$ taken together form a polymethylene bridge having 2 to 10 carbon atoms; R is alkylene having 1 to 6 carbon atoms, alkenylene having 3 to 8 carbon atoms, cycloalkylene having 5 to 6 carbon atoms, aralkylene hydrocarbon having 7 to 14 carbon atoms or arylene hydrocarbon having 6 to 12 carbon atoms or R is one of said radicals substituted by chlorine, bromine, nitro, alkyl having 1 to 4 carbon atoms, phenoxy or alkoxy having 1 to 4 carbon atoms, said process comprising the steps of reacting a carbamic acid chloride of the formula

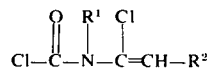

with an amine of the formula $$H_2N - R - NH_2$$

in the presence of an alkali metal hydroxide at a temperature of from 5° to 60°C. and in a molar ratio of 2 mols of said carbamic acid chloride reactant and 2 mols of said alkali metal hydroxide per mol of said amine reactant and then hydrolyzing the resulting intermediate at a temperature of from 20° to 100°C. to obtain said substituted urea of said formula.

2. The process of claim 1 wherein $R^1$ taken separately is alkyl having 1 to 4 carbon atoms, alkenyl having 3 to 4 carbon atoms, cycloalkyl having 5 to 6 carbon atoms or phenyl; $R^2$ taken separately is hydrogen, alkyl having 1 to 8 carbon atoms, alkenyl having 2 to 8 carbon atoms, benzyl, phenethyl or phenyl or $R^1$ and $R^2$ taken together form a polymethylene bridge having 4 to 6 carbon atoms, R is alkylene having 1 to 6 carbon atoms, alkenylene having 3 to 4 carbon atoms, cycloalkylene having 5 to 6 carbon atoms, aralkylene having 7 to 14 carbon atoms or phenylene or R is one of said radicals substituted by chlorine, bromine, nitro, alkyl having 1 to 4 carbon atoms, phenoxy or alkoxy having 1 to 4 carbon atoms.

3. The process of claim 1 wherein said hydrolyzing step is carried out in the presence of alkali metal hydroxide as hydrogen chloride acceptor.

4. The process of claim 1 wherein $R^1$ and $R^2$ are taken together and are a polymethylene bridge having 4 carbon atoms and R is $- CH_2 - CH_2 - CH_2 - CH_2 - CH_2 - CH_2 -$.

* * * * *